United States Patent
Homan et al.

(10) Patent No.: US 8,942,442 B2
(45) Date of Patent: Jan. 27, 2015

(54) METHOD AND DEVICE FOR ALIGNING A NEEDLE

(75) Inventors: Robert Johannes Frederik Homan, Best (NL); Drazenko Babic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 928 days.

(21) Appl. No.: 13/057,481

(22) PCT Filed: Aug. 4, 2009

(86) PCT No.: PCT/IB2009/053373
§ 371 (c)(1),
(2), (4) Date: Mar. 21, 2011

(87) PCT Pub. No.: WO2010/015994
PCT Pub. Date: Feb. 11, 2010

(65) Prior Publication Data
US 2011/0158479 A1    Jun. 30, 2011

(30) Foreign Application Priority Data
Aug. 8, 2008   (EP) .................................... 08162048

(51) Int. Cl.
*G06K 9/00*  (2006.01)
*H04N 7/18*  (2006.01)
(Continued)

(52) U.S. Cl.
CPC ........... *A61B 17/3403* (2013.01); *A61B 19/201* (2013.01); *A61B 19/525* (2013.01); *A61B 2017/3405* (2013.01); *A61B 2017/3411* (2013.01); *A61B 2019/5238* (2013.01)
USPC ............. 382/128; 348/77; 382/100; 604/510; 600/114; 600/434

(58) Field of Classification Search
USPC ......... 382/100, 103, 128–133, 153, 286–287; 600/300, 309, 407, 417, 429, 431, 600/436–464, 471–472; 606/1, 41–46, 130
See application file for complete search history.

(56) References Cited

U.S. PATENT DOCUMENTS 4,485,815 A   12/1984   Amplatz et al.
4,917,111 A    4/1990   Pennig et al.
(Continued)

FOREIGN PATENT DOCUMENTS

JP    2007190199 A    8/2007

OTHER PUBLICATIONS

Boctor et al.,"Three-Dimensional Ultrasound-Guided Robotic Needle Placement: An Experimental Evaluation"; Interntational Journal Med Robotics Comput Assist Surg 2008; 4: pp. 180-191, Wiley InterScience.*
(Continued)

*Primary Examiner* — Randolph I Chu
*Assistant Examiner* — Nathan Bloom

(57) ABSTRACT

A method and a device for use in conjunction with an imaging modality (202), for controlling the angular orientation of a needle-shaped object (212) while moving it along a path (214) from a given entry point to a given target point in a body during a percutaneous intervention. The device comprises a support unit (502, 602, 702, 802) for supporting a guiding unit (506, 706), which support unit provides a pair of parallel control planes (604, 606) which are at least partially detectable by the imaging modality. The guiding unit establishes a guiding axis (612, 818) substantially perpendicular to the pair of parallel control planes along which guiding axis the needle-shaped object is translatable. The angular orientation of an imaging plane (204) applied by the imaging modality determines a reference for the angular orientation of the pair of parallel control planes. By aligning the pair of parallel control planes with the imaging plane, the guiding axis is in correlation with the path from the entry point to the target point.

20 Claims, 5 Drawing Sheets

(51) Int. Cl.
*A61M 31/00* (2006.01)
*A61B 1/04* (2006.01)
*A61B 1/00* (2006.01)
*A61B 6/00* (2006.01)
*A61M 25/00* (2006.01)
*A61B 17/34* (2006.01)
*A61B 19/00* (2006.01)

(56) References Cited

U.S. PATENT DOCUMENTS

| | | | |
|---|---|---|---|
| 6,487,431 | B1 | 11/2002 | Iwano et al. |
| 7,346,385 | B2 | 3/2008 | Bascle et al. |
| 2002/0156369 | A1* | 10/2002 | Chakeres .................. 600/422 |
| 2003/0114862 | A1 | 6/2003 | Chu et al. |
| 2003/0120283 | A1* | 6/2003 | Stoianovici et al. .......... 606/130 |
| 2004/0220444 | A1 | 11/2004 | Hogendijk et al. |
| 2006/0064010 | A1* | 3/2006 | Cannon et al. ................ 600/434 |
| 2007/0135708 | A1 | 6/2007 | Chu et al. |
| 2008/0095422 | A1* | 4/2008 | Suri et al. ..................... 382/131 |
| 2009/0030339 | A1* | 1/2009 | Cheng et al. ................. 600/562 |
| 2009/0227863 | A1* | 9/2009 | Bzostek et al. .............. 600/424 |

OTHER PUBLICATIONS

Reed, Kyle B., et al. "Integrated planning and image-guided control for planar needle steering." Biomedical Robotics and Biomechatronics, 2008. BioRob 2008. 2nd IEEE RAS & EMBS International Conference on. IEEE, 2008.*

Patriciu, Alexandru, et al. "Motion-based robotic instrument targeting under C-Arm fluoroscopy." Medical Image Computing and Computer-Assisted Intervention-MICCAI 2000. Springer Berlin Heidelberg, 2000.*

* cited by examiner

METHOD AND DEVICE FOR ALIGNING A NEEDLE

FIELD OF THE INVENTION

The invention relates to a method for use in conjunction with an imaging modality, for guiding a needle-shaped object along a path connecting a given entry point and a given target point in a body during percutaneous interventions. The invention further relates to a device for performing said method.

BACKGROUND OF THE INVENTION

US-A 2007/0135708 discloses a needle guiding device utilized by a medical professional to guide a needle towards a target along a needle insertion trajectory. A method that utilizes a fluoroscope can be used to locate the target. The needle guiding device is at least partially constructed form radiopaque material, and is visible in the fluoroscope display when it is positioned in a fluoro-axis beam emitted by a fluoroscope emitter towards a fluoroscope receiver. The medical professional utilizes knowledge of the relative positioning of the needle guiding device and the fluoro-axis beam to guide the needle towards the target.

The techniques disclosed in US-A 2007/0135708 are not capable of controlling the angular orientation of the needle in a three dimensional space while moving the needle from an entry point to a target point.

The known techniques map information regarding the needle's angular orientation from a three dimensional space onto a two dimensional space, namely the viewing plane by which the physician is tracking the needle's progress. Rotations of the needle with respect to an axis parallel to or contained in the viewing plane, are not detectable distinguishable in the viewing plane, hence remain uncontrollable for the physician. This may result in a deviation of the needle with respect to the path from the entry point and the target point. Consequently, vital organs may be damaged by the needle.

SUMMARY OF THE INVENTION

It is an object of the invention to provide a method for controlling the angular orientation of a needle-shaped object in a three-dimensional space for the purpose of correctly moving the needle-shaped object along a path from an entry point to a target point in a body.

This object is achieved by the method according to the invention, which is characterized by the step of installing a support unit in the proximity of the body, which support unit provides a pair of parallel control planes and which support unit is arranged for supporting a guiding unit, which guiding unit determines a guiding axis for guiding the needle-shaped object, which guiding axis is substantially perpendicular, particularly perpendicular, to said pair of parallel control planes, the step of applying an imaging plane by the imaging modality, wherein the angular orientation of the imaging plane determines a reference for the angular orientation of the pair of parallel control planes, which imaging plane is perpendicular to the path from the entry point to the target point, the step of detecting a deviation between the angular orientations of the pair of parallel control planes and the imaging plane by the imaging modality, the step of aligning the guiding axis with the path from the entry point to the target point by aligning the pair of parallel control planes with the imaging plane, and the step of translating the needle-shaped object along the guiding axis.

Here, an imaging modality implies a medical imaging device capable of providing a two-dimensional projection in a direction substantially perpendicular to the progression direction of the needle-shaped object, such as an x ray device. Installing the support unit in the proximity of the body includes installing the support unit on the body. Herein the support body may be installed such that it entirely tangents to the body. Alternatively, the support unit rests against the body on at least three positions, possibly with the help of additional support members.

As mentioned before, the imaging modality applies an imaging plane. The imaging plane extends from a focus towards a detector of the imaging modality.

The orientation of the imaging plane acts as a reference for the orientation of the pair of parallel control planes. Herein, the orientation of the imaging plane is such that the imaging plane is substantially perpendicular to the path from the entry point to the target point. Namely, the guiding axis and the pair of parallel planes are mutually substantially perpendicular. Hence, if the imaging plane is applied substantially perpendicular to the aforementioned path, the guiding axis logically corresponds to the path from the entry point to the target point in case the orientation of the pair of parallel planes corresponds to the orientation of the imaging plane.

By employing the display of the imaging modality, the medical professional is able to verify whether or not the orientations associated with the pair of parallel planes and the imaging plane are coinciding. Namely, the parallel control planes are at least partially detectable by the imaging modality. That is, the parallel control planes are at least partially manufactured from a radiopaque material, or alternatively, they are at least partially supplied with a radiopaque paint. Herein, radiopaque refers to the ability of a substance to prevent the passage of electromagnetic radiation there through. In case the pair of parallel control planes with the imaging plane, hence in case the pair of parallel control planes attains a correct angular orientation, a side view of the support unit will be visible in the display of the imaging modality as a sharply outlined surface. A deviation between the angular orientation of the pair of parallel control planes and the angular orientation of the imaging plane is effectively detectable. Namely, rotations of the pair of parallel control planes with respect to an axis having at least a component parallel to the imaging plane or contained in the imaging plane will cause the sharply outlined surface to transform into a surface having substantially blurry curved edges. Owing to the pair of parallel control planes, the visibility of a deviation between the orientation of the imaging plane and the orientation of the pair of parallel planes is magnified to a large extend. The latter quality enables a medical professional to detect said deviation. Subsequently, the medical professional rectifies the angular orientation of the pair of parallel control planes through manually handling the support unit. For this purpose, the medical professional can interactively employ the real time visual feedback provided by the display of the imaging modality.

By matching the orientations of the pair of parallel control planes and the imaging plane, the guiding axis is aligned with the path from the entry point to the target point. By subsequently translating the needle-shaped object along the guiding axis, the needle-shaped object correctly moves along the path from the entry point to the target point. Herein the guiding unit assures that the needle-shaped object's movement does correspond to the guiding axis and consequently to said path from the entry point to the target point.

The method according to the invention protects the operator from multiple incidence modifications of the imaging plane's position and orientation in order to assess the correctness of the needle-shaped object's orientation with respect to the path connecting the entry point and the target point. The continuous changing of e.g. a C-arm geometry in case of rotational x ray, is experienced to be extremely tedious and labor intensive. Hence, the method according to the invention not only provides effective control for a needle-shaped object's angular orientation, it additionally provides an efficient and intuitively way of working for the medical professional.

In an embodiment of the method according to the invention, the needle-shaped object is inserted into the guiding unit. Hence, the needle need not necessarily be already contained in the guiding unit.

It is a further object of the invention to provide a device for controlling the angular orientation of a needle-shaped object in a three-dimensional space for the purpose of correctly moving the needle-shaped object along a path from an entry point to a target point in a body.

This object is achieved by the device according to the invention, which is characterized by a support unit for supporting a guiding unit, which support unit provides a pair of parallel control planes which are at least partially detectable by the imaging modality, which guiding unit establishes a guiding axis along which the needle-shaped object is translatable, and which guiding axis is substantially perpendicular, particularly perpendicular, to said pair of parallel control planes. Detectability of the pair of parallel control planes by the imaging modality is accomplished by at least partially manufacturing the parallel control planes from a radiopaque material or by at least partially supplying them with a radiopaque paint. The guiding unit is constructed in such a way that the needle-shaped object is guaranteed to be movable along the guiding axis only.

In an embodiment of the device according to the invention, the support unit defines a guiding aperture.

In a further embodiment of the device according to the invention, the support unit is substantially flat. As a result, the detectability of deviations between the orientation associated with the imaging plane and the orientation of the pair of parallel control planes is enhanced. Namely, the substantially flat geometry of the support unit will magnify the visibility of a rotation from the pair of parallel control planes with regard to an axis contained in or parallel to the imaging plane.

In a further embodiment of the device according to the invention, the support unit is a uniformly disc-shaped body. Herein, a body is considered to be disc-shaped in case the ratio of its radius and its thickness exceeds 10. A deviation between the orientation of the pair of parallel control planes defined by the sides of the disc shaped body and the orientation of the imaging plane is unambiguously detectable by the medical professional by having a look at the display comprised by the imaging modality. Namely, in case the pair of parallel control planes is aligned with the imaging plane, a sharply outlined rectangular surface will be visible. A deviation will cause the sharply outlined rectangular surface to become a blurry edged ellipse shaped surface.

In a further embodiment of the device according to the invention, the guiding axis extends through the center of gravity of the uniform disc.

In a further embodiment of the device according to the invention, the guiding unit comprises a guiding cylinder, which guiding cylinder envelops the guiding axis and which guiding cylinder has a guiding diameter matching a needle-shaped object's diameter. Herein, the guiding diameter is slightly larger than the needle-shaped object's diameter. On the one hand, the guiding cylinder is to guarantee that the needle-shaped object translates along the guiding axis in a well defined and reproducible manner, on the other hand, the guiding cylinder is to provide a sufficiently small level of friction in order to allow the physician to smoothly move the needle-shaped object along the guiding axis.

In a further embodiment of the device according to the invention, the guiding unit comprises a further guiding axis.

In a further embodiment of the device according to the invention, the guiding unit comprises a further guiding cylinder, which further guiding cylinder envelops the further guiding axis and which further guiding cylinder has a further guiding diameter matching a further needle-shaped object's diameter. As a result, the guiding unit allows for guiding needle-shaped objects having various diameters.

It is a further object of the invention to provide a system for controlling the angular orientation of a needle-shaped object in a three-dimensional space for the purpose of correctly moving the needle-shaped object along a path from an entry point to a target point in a body.

This object is achieved by the system according to the invention which comprises an imaging modality and the device according to the invention.

DETAILED DESCRIPTION OF THE EMBODIMENTS

Figure 1:
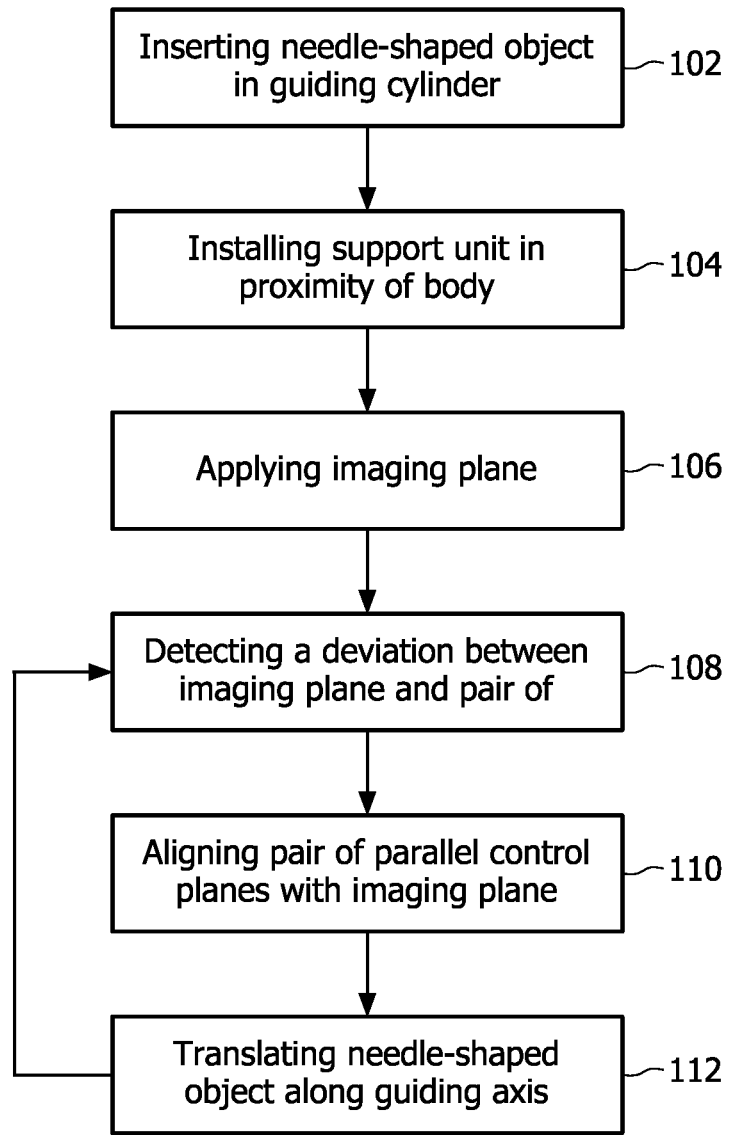
FIG. 1 schematically displays an embodiment of the method according to the invention.

FIG. 1 displays a flowchart representing an embodiment of the method according to the invention. The method is arranged for moving a needle-shaped object along a path from a given entry point to a given target point in a body during percutaneous interventions. A first step 102 comprises inserting the needle-shaped object in a guiding cylinder comprised in a guiding unit, which guiding unit is supported by a support unit. Prior to this, both the needle-shaped object and the support unit together with the guiding unit, or at least the guiding unit, must be unshelled from their sterile packaging. A second step 104 comprises installing the needle-shaped object at the entry point and subsequently installing the support unit in the proximity of the body. It is noted that the step 102 and the step 104 may be exchanged with one another, i.e.

the support body may be installed in the proximity of the body prior to inserting the needle-shaped object in the guiding cylinder. A third step 106 comprises applying an imaging plane by an imaging modality such as x ray. As explained before, the orientation of the imaging plane provides a reference for the angular orientation of the pair of parallel control planes determined by the support unit. Herein the imaging plane is applied perpendicular to the path from the entry point to the target point, given the perpendicular orientation of the guiding axis with respect to the pair of parallel control planes.

Figure 2:
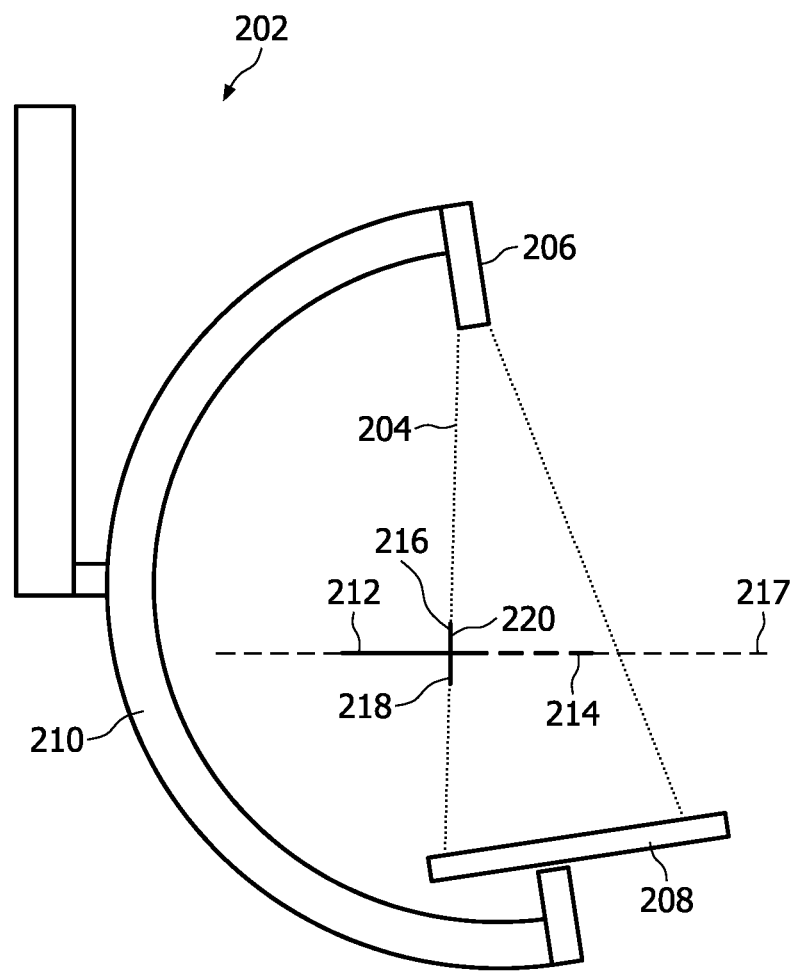
FIG. 2 schematically depicts an application of an imaging plane on a rotational x ray device on the basis of a specific path from an entry point to a target point.

FIG. 2 schematically displays a rotational x ray device 202 applying an imaging plane 204 which extends from a focus 206 towards a detector 208. The rotational x ray device comprises a C arm 210 which is arranged for determining the angular orientation of the imaging plane 204. A needle-shaped object 212 is to be moved along a path 214. A support unit 216 is arranged for supporting a guiding unit (not shown in FIG. 2), which guiding unit determines a guiding axis 217. The support unit 216 is provided with a pair of parallel planes 218 and 220. As explained before, the guiding axis 217 and the pair of parallel control planes 218 and 220 are mutually perpendicular. The imaging plane 204 is applied such that it is perpendicular to the path 214. Apparently, in FIG. 2 the imaging plane 204 and the pair of parallel control planes 218 and 220 are aligned with one another. Consequently, the needle-shaped object 212 will correctly move along the path 214.

Referring to FIG. 1, a fourth step 108 comprises detecting a deviation between the angular orientations of the pair of parallel control planes and the imaging plane. As explained before, in case the pair of parallel control planes is aligned with the imaging plane, the support unit will be visible in a display comprised in the imaging modality as a sharply outlined surface.

Figure 3:
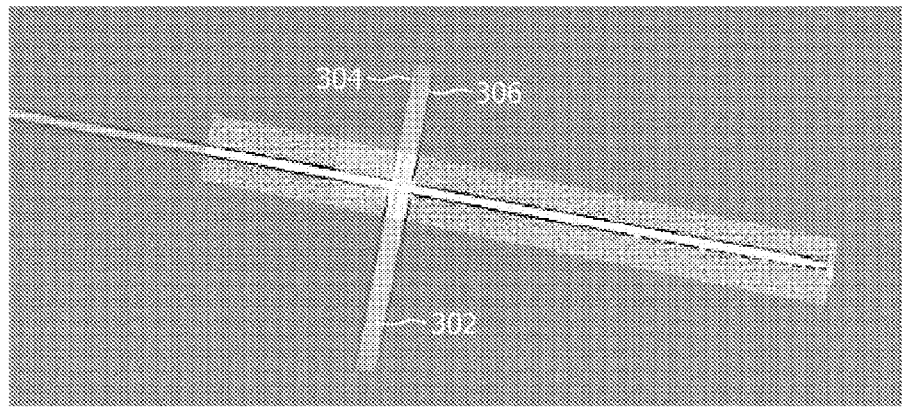
FIG. 3 shows a support unit as seen on a display comprised in an imaging modality, in case the pair of parallel control planes provided by the device according to the invention is aligned with the imaging plane.

FIG. 3 shows a support unit 302 as seen on a display comprised in an imaging modality in case the pair of parallel control planes 304 and 306 is aligned with the imaging plane. Herein, the support unit 302 is embodied by a disc-shaped body. Clearly, a side of the support unit 302 is visible as a sharply outlined rectangular surface.

Figure 4:
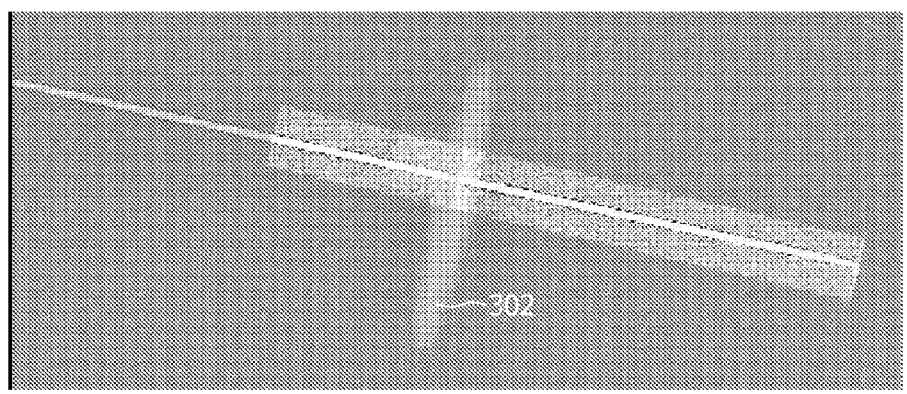
FIG. 4 depicts a support unit as seen on a display comprised in an imaging modality in case there is a visible deviation between the angular orientations of the imaging plane and the pair of control planes determined by the device according to the invention.

FIG. 4 depicts the support unit 302 as seen on a display comprised in the imaging modality in case there is a visible deviation between the angular orientations of the imaging plane and the pair of control planes 304 and 306. Clearly, the sharply outlined rectangular surface has transformed into a blurry edged ellipse shaped surface through a rotation of the pair of parallel control planes 304 and 306 with regard to an axis contained in or a parallel to the imaging plane.

Referring to FIG. 1, a fifth step 110 comprises aligning the pair of parallel control planes with the imaging plane manually by the medical professional on the basis of the real time visual feedback provided by the display of the imaging modality. A sixth step 112 comprises moving the needle-shaped object along the guiding axis by translating it through the guiding cylinder comprised in the guiding unit. Meanwhile, the occurrence of deviations between the angular orientations of the imaging plane and the pair of parallel control planes is verified at the step 108.

Figure 5:
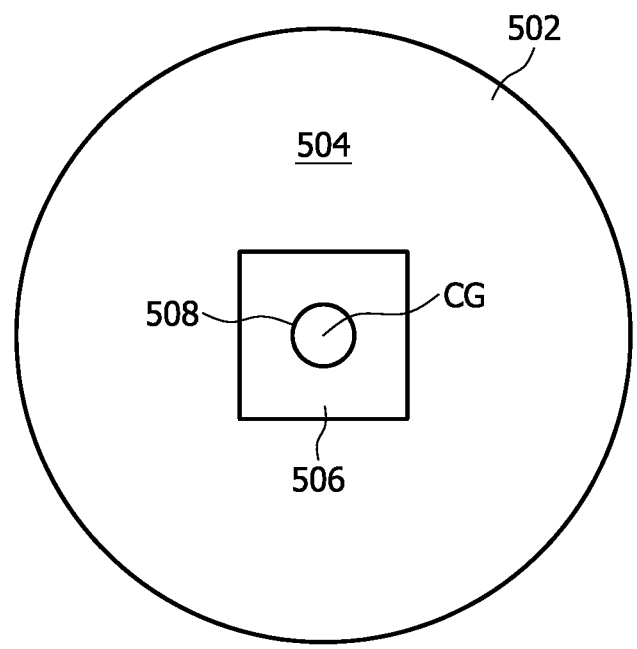
FIG. 5 schematically depicts a first embodiment of the device according to the invention in frontal view.

FIG. 5 displays a plan view of a first embodiment of the device according to the invention. Herein, the support unit 502 is a disc shaped body. The support unit 502 determines a pair of parallel control planes, of which plane 504 is shown. The disc shaped body 502 is manufactured from a radiopaque material as to guarantee the visibility for the pair of parallel control planes in a display comprised in an imaging modality. The disc shaped body 502 supports a guiding unit 506. The guiding unit 506 comprises a guiding cylinder 508 which determines a guiding axis (not shown in FIG. 5) extending through the centre of gravity CG of the support unit 502.

Figure 6:
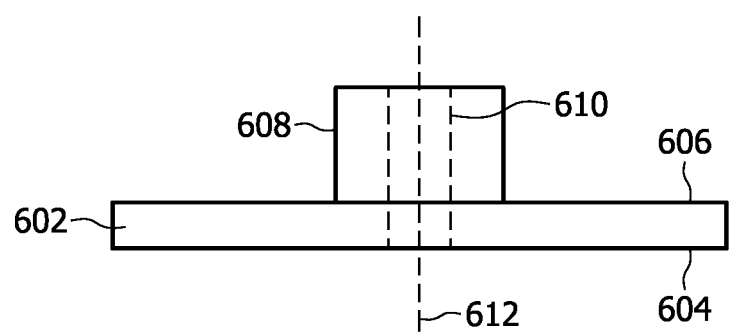
FIG. 6 schematically shows the first embodiment of the device according to the invention in side view.

FIG. 6 depicts a side view of the first embodiment according to the invention. A support unit 602 defines a pair of parallel control planes 604 and 606. The control plane 604 is most suitable to be installed in the proximity of or at the body. A guiding unit 608 is attached to the support unit 602. The guiding unit 608 comprises a guiding cylinder 610 which determines a guiding axis 612 perpendicular to the pair of parallel control planes 604 and 606.

Figure 7:
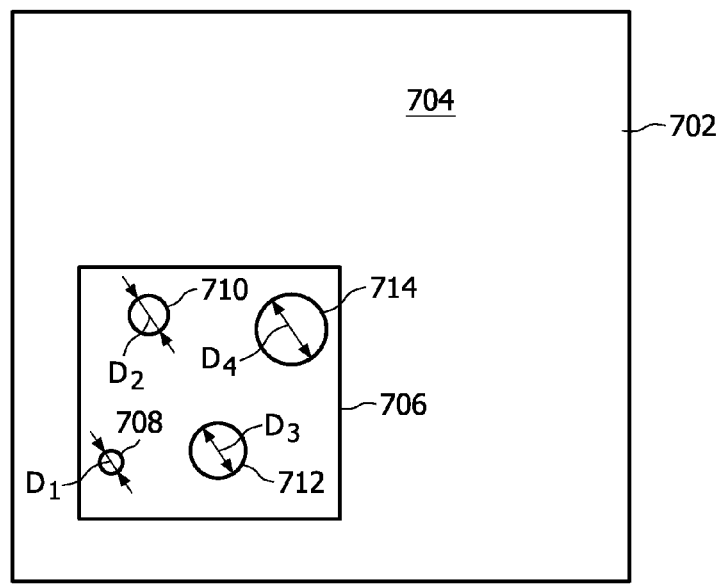
FIG. 7 schematically depicts a second embodiment of the device according to the invention in frontal view.

FIG. 7 displays a plan view of a second embodiment of the device according to the invention. Herein, the support unit 702 is a substantially flat rectangular shaped body. The support unit 702 determines a pair of parallel control planes, of which 704 is shown. The pair of parallel control planes are supplied by radiopaque paint for the purpose of visibility in a display comprised in an imaging modality. The support unit 702 supports a guiding unit 706. The guiding unit 706 comprises a plurality of guiding cylinders, in this example four cylinders, 708, 710, 712 and 714 having guiding diameters $D_1$, $D_2$, $D_3$ and $D_4$, respectively. Herein it holds that $D_1<D_2<D_3<D_4$. As a result the guiding unit allows for guiding needle-shaped objects having various needle-shaped objects'-diameters, namely needle-shaped objects'-diameters matching the guiding diameters $D_1$, $D_2$, $D_3$ and $D_4$.

Figure 8:
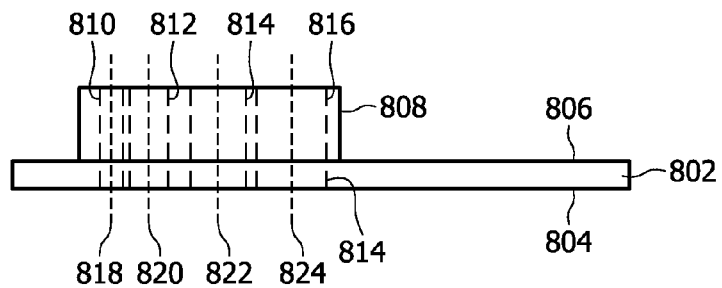
FIG. 8 schematically shows the second embodiment of the device according to the invention in side view.

FIG. 8 depicts a side view of the second embodiment of the device according to the invention. A substantially flat support unit 802 defines a pair of parallel control planes 804 and 806. The control plane 804 is to be installed in the proximity of or at the body. A guiding unit 808 is attached to the support unit 802. The guiding unit 808 comprises a plurality of guiding cylinders 810, 812, 814 and 816 having guiding diameters $D_1$, $D_2$, $D_3$ and $D_4$, respectively. The guiding cylinders 810, 812, 814 and 816 determine guiding axes 818, 820, 822 and 824, respectively. All guiding axes 818, 820, 822 and 824 are perpendicular to the pair of parallel control planes.

Figure 9:
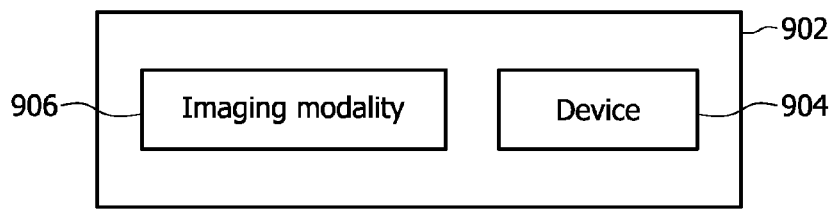
FIG. 9 schematically displays an embodiment of the system according the invention.

FIG. 9 displays an embodiment of the system according to the invention. The system 902 comprises a device 904 according to the invention and an imaging modality 906 such as an x ray device.

While the invention has been illustrated and described in detail in the drawings and in the foregoing description, the illustrations and the description are to be considered illustrative or exemplary and not restrictive. The invention is not limited to the disclosed embodiments. It is noted that the device to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A system comprising:
   a configuration based on an imaging modality;
   an imaging device for controlling an angular orientation of
      a needle-shaped object while moving it along a path
      from a given entry point to a given target point in a body
      during a percutaneous intervention, said device comprising
      a guiding unit; and
      a support unit for supporting the guiding unit, which
         support unit provides a pair of parallel control planes
         which are at least partially detectable by the imaging
         modality, wherein the guiding unit establishes a guiding axis along which the needle-shaped object is translatable, and wherein the guiding axis is substantially perpendicular to said pair of parallel control planes, and which imaging-modality-based configuration has a focus and includes a detector,
wherein the system is configured for:
installing the support unit in the proximity of the body;
applying an imaging plane of the imaging modality, wherein the angular orientation of the imaging plane determines a reference for the angular orientation of the pair of parallel control planes, which imaging plane extends from the focus towards the detector and is perpendicular to said path; and
detecting a deviation between the angular orientations of the pair of parallel control planes and said imaging plane, by providing a side view of the support unit for bringing the guiding axis in correlation with said path by aligning the pair of parallel control planes with the imaging plane.

2. The system according to claim 1, wherein the support unit defines a guiding aperture.

3. The system according to claim 1 wherein the support unit is substantially flat.

4. The system according to claim 1 wherein the support unit is a uniformly disc-shaped body.

5. The system according to claim 4, wherein the guiding axis extends through the center of gravity of the uniformly disc-shaped body.

6. The system according to claim 1, wherein the guiding unit comprises a guiding cylinder, which guiding cylinder envelops the guiding axis and which guiding cylinder has a guiding diameter matching a needle-shaped object's diameter.

7. The system according to claim 6, wherein the guiding unit establishes a further guiding axis.

8. The system according to claim 7, wherein the guiding unit comprises a further guiding cylinder, which further guiding cylinder envelops the further guiding axis and which further guiding cylinder has a further guiding diameter matching a further needle-shaped object's diameter.

9. A device for controlling an angular orientation of a needle-shaped object while attempting to move said object along a path from a given entry point to a given target point in a body during a percutaneous intervention, said device comprising:
a display;
an imaging processor; and
a support unit for supporting a guiding unit, which support unit provides a pair of parallel control planes through which the guiding unit establishes a guiding axis along which a needle-shaped object is translatable, and wherein the guiding axis is substantially perpendicular to said pair of parallel control planes, which are at least partially detectable by the imaging modality,
said imaging processor being configured for providing:
via said display and in a viewing direction perpendicular to said path, a side view of the support unit; and,
via said display and in said direction as the translating occurs, a depiction of a representation of an angular deviation of said pair of parallel control planes from said direction to enable corrective alignment of said pair of parallel control planes to said direction.

10. The device according to claim 9, configured such that, during the translation, a change in a visual characteristic of the depicted representation indicative of an increase in said deviation is interactively reversible by the aligning following interruption of said translation.

11. The device according to claim 9, wherein the support unit is substantially flat.

12. The device according to claim 9, wherein the support unit is a uniformly disc-shaped body.

13. The device of claim 12, said body having a radius and thickness, a ratio of said radius to said thickness exceeding 10.

14. The device according to claim 12, wherein the guiding axis extends through the center of gravity of the uniformly disc-shaped body.

15. The device according to claim 9, said object having a diameter, said guiding unit comprising a guiding cylinder, which guiding cylinder envelops the guiding axis and which guiding cylinder has a guiding diameter matching said diameter.

16. The device according to claim 15, wherein the guiding unit establishes a further guiding axis.

17. The device according to claim 16, wherein the guiding unit comprises a further guiding cylinder, which further guiding cylinder envelops the further guiding axis and which further guiding cylinder has a further guiding diameter matching a further needle-shaped object's diameter.

18. The device of claim 9, said parallel control planes defining a region that includes radiopaque material.

19. The device of claim 9, configured for, via said display, providing real time visual feedback via said representation.

20. A device for controlling an angular orientation of a needle-shaped object while attempting to move said object along a path from a given entry point to give target point in a body during a percutaneous intervention, said device comprising:
a display;
an imaging processor; and
a support unit for supporting a guiding unit, which support unit provides a pair of parallel control planes through which the guiding unit establishes a guiding axis along which a needle-shaped object is translatable, and wherein the guiding axis is substantially perpendicular to said pair of parallel control planes, which are at least partially detectable by the imaging modality,
said imaging processor being configured for providing:
via said display and in a viewing direction perpendicular to said path, a side view of the support; and,
via said display and in said direction as the translating occurs, a depiction of a representation of an angular deviation of said pair of parallel control planes from said direction to enable corrective alignment of said of parallel control planes to said direction, said device being configured such that sharpness of said depiction decreases with said deviation.

\* \* \* \* \*